(12) United States Patent
Kim et al.

(10) Patent No.: US 12,030,850 B2
(45) Date of Patent: Jul. 9, 2024

(54) METHOD FOR PRODUCING ESTER BASED ON ECO-FRIENDLY AND HIGH-EFFICIENCY ESTERIFICATION BY USING BASE EXCHANGE OF SALT AND THE COMPOUND THEREOF

(71) Applicant: Woodward Bio Corp., Incheon (KR)

(72) Inventors: Gab Yong Kim, Incheon (KR); Seong Eun Lee, Seoul (KR)

(73) Assignee: WOODWARD BIO CORP., Incheon (KR)

( * ) Notice: Subject to any disclaimer, the term of this patent is extended or adjusted under 35 U.S.C. 154(b) by 0 days.

(21) Appl. No.: 17/107,037

(22) PCT Filed: Nov. 24, 2020

(86) PCT No.: PCT/KR2020/016740
§ 371 (c)(1),
(2) Date: Nov. 30, 2020

(87) PCT Pub. No.: WO2022/097813
PCT Pub. Date: May 12, 2022

(65) Prior Publication Data
US 2023/0265039 A1    Aug. 24, 2023

(30) Foreign Application Priority Data

Nov. 5, 2020 (KR) .................. 10-2020-0146843

(51) Int. Cl.
C07C 67/08 (2006.01)
C07C 277/08 (2006.01)
C07C 279/14 (2006.01)

(52) U.S. Cl.
CPC ............ *C07C 67/08* (2013.01); *C07C 277/08* (2013.01); *C07C 279/14* (2013.01); *C07C 2601/14* (2017.05)

(58) Field of Classification Search
CPC ...... C07C 67/08; C07C 277/08; C07C 279/14
See application file for complete search history.

(56) References Cited

U.S. PATENT DOCUMENTS 7,087,769 B1    8/2006   Contijoch Mestres
8,278,478 B2   10/2012   Ghare
(Continued)

FOREIGN PATENT DOCUMENTS

| CN | 110938020 A | 3/2020 | |
| KR | 10-2020-0108764 A | 9/2020 | |
| WO | WO 2020/184797 | * 9/2020 | ........... C07C 277/08 |

OTHER PUBLICATIONS

Prutton, C.F., et al., The system calcium chloride-magnesium chloride water At),-15 and -30 degrees, Journal of the American Chemical Society, vol. 54, issue 8, (pp. 3025-3468), pp. 3040-3047 (Year: 1932).*

(Continued)

*Primary Examiner* — Yate' K Cutliff
(74) *Attorney, Agent, or Firm* — Studebaker & Brackett PC

(57) ABSTRACT

Provided are an environmentally-friendly high-efficiency method of manufacturing an ester compound based on an esterification reaction using a salt ion-exchange method and an ester compound manufactured thereby. In the conventional esterification reaction, an ester was produced in low yields due to the hydrolysis (i.e., reverse reaction) caused by water, or it was required to continuously supply hydrochloric acid gas or use thionyl chloride, which is a hazardous material, and thus there were limitations in terms of environmental friendliness or cost. On the other hand, in the present invention, hydrochloric acid gas is continuously supplied using the salt ion-exchange method, and since magnesium sulfate acts as a dehydrating agent, the water generated in the esterification reaction is removed, and thus (Continued)

the occurrence of hydrolysis (i.e., reverse reaction) is suppressed and a conversion rate to the desired ester compound is increased. In addition, since the reactants are inexpensive and the product is less hazardous and easy to handle, a more efficient reaction is possible.

6 Claims, 6 Drawing Sheets

(56) References Cited

U.S. PATENT DOCUMENTS

2011/0077423 A1* 3/2011 Ghare .................. C07C 277/08
560/169
2017/0355609 A1* 12/2017 Fournier ................ C01G 53/04

OTHER PUBLICATIONS

An Office Action; "Notice of Reasons for Refusal," mailed by the Japanese Patent Office on Mar. 20, 2023, which corresponds to Japanese Patent Application No. 2020-568377 and is related to U.S. Appl. No. 17/107,037.
International Search Report issued in PCT/KR/2020/016740; mailed Jul. 30, 2021.
Written Opinion issued in PCT/KR/2020/016740; completed Jul. 30, 2021.

* cited by examiner

METHOD FOR PRODUCING ESTER BASED ON ECO-FRIENDLY AND HIGH-EFFICIENCY ESTERIFICATION BY USING BASE EXCHANGE OF SALT AND THE COMPOUND THEREOF

TECHNICAL FIELD

The present invention relates to an ester compound manufacturing method based on an environmentally-friendly high-efficiency esterification reaction using a salt ion-exchange method and a compound manufactured thereby. More particularly, the present invention relates to: an ester compound manufacturing method which uses an environmentally-friendly esterification reaction through ion-exchange between an alkali metal salt and an alkaline earth metal salt constituting seawater and is capable of manufacturing a non-toxic ester compound in high yields without generating hazardous waste; and an application of an ester compound manufactured by the manufacturing method.

BACKGROUND ART

An esterification reaction is a dehydration reaction occurring between an alcohol and an organic acid, in which water is removed and an ester compound is formed, and the esterification reaction is applied to a variety of industries and widely used in high value-added basic chemical material industries such as pharmaceuticals, fragrances, and biodiesel.

In general, the esterification reaction is performed using an acid catalyst such as sulfuric acid, phosphoric acid, hydrochloric acid, or p-toluenesulfonic acid or a catalyst for inducing acyl-chlorination or alkyl-chlorination, such as thionyl chloride.

A representative acid-catalyzed esterification reaction is Fischer esterification, which is a reaction in which an excessive amount of alcohol and an organic acid are reacted in the presence of an acid catalyst to produce an ester compound. Sulfuric acid is used for this reaction in most cases, and since the esterification reaction is a reversible reaction, there are cases in which the product, an ester, is hydrolyzed (i.e., reversely reacted) by the water produced by the same reaction, resulting in a very low conversion rate to the ester.

As another method, hydrochloric acid may be used as an acid catalyst, but this is not desirable because hydrochloric acid in a gaseous form should be used and when an aqueous hydrochloric acid solution is used, a reaction with water is inevitable, and the product is eventually hydrolyzed (i.e., reversely reacted) by water. Moreover, since hydrochloric acid gas volatilizes at high temperatures, there is a hassle of having to continuously add the gas to proceed with the reaction.

The above-described problems may be solved using thionyl chloride, which is widely used because of a simple process and high reactivity. However, thionyl chloride is a toxic and corrosive material that can react violently with water or an alcohol and cause an explosion, and when more alcohol or water is added to remove thionyl chloride upon completion of a reaction, sulfur dioxide, which is one of the main air pollutants, is generated. Moreover, there are disadvantages that equipment is corroded during the removal process and the removal process is time-consuming.

As such, the disadvantage that the above two types of esterification reactions have in common is that the water produced in the dehydration process should be removed.

The Fischer esterification reaction is a reversible reaction as described above, and according to Le Chatelier's principle, water should be removed in order to induce a forward reaction and increase a conversion rate to an ester compound. Therefore, a dehydrating agent is needed, but it is difficult to find a combination of dehydrating agents that is compatible with all the solvents, and there may be cases in which the alcohol structure is converted into an ether structure due to the dehydration of the solvents. In this case, since the number of alcohol molecules that can participate in a reaction decreases and thus the probability of occurrence of the reaction decreases, a conversion rate to an ester compound decreases.

Even an acid-catalyzed esterification reaction has the disadvantage that it is difficult to remove a residual acid catalyst depending on the structure and characteristics of the produced ester compound. In the case of products having low polarity, the acid can be removed through an extraction method, but in the case of products having high polarity and thus having high affinity with water, it is very difficult to separate the acid. Moreover, as in the case of an amino acid, when an amine group is present, since the product forms a salt with the acid catalyst, it is required that a separate purification process such as desalting is performed to produce the desired salt. In addition, in the case of a general ester compound having an amine group, a hydrochloride is typically produced, and when a sulfuric acid-based acid catalyst is used, there is the difficulty of purification due to the difficulty of desalting.

Although various esterification reaction methods have been developed to prevent the generation of the above-described environmentally hazardous materials in an esterification reaction, improve the difficulty of purification, and increase an esterification conversion rate, since an expensive catalyst is used and thus raw material costs are increased, there is an increasing need to develop an environmentally-friendly high-efficiency esterification reaction.

DISCLOSURE

Technical Problem

The present invention is directed to providing a high value-added ester compound suitable for commercialization by developing a reaction which is performed using an environmentally-friendly, highly efficient, and inexpensive esterification reaction catalyst and various organic acids and alcohols and has a high conversion rate to an ester compound.

By developing the reaction and providing the ester compound, the present invention is directed to reducing industrial waste while securing biodegradability, safety, low toxicity, and economic efficiency, and further, reducing environmental pollution.

Technical Solution

One aspect of the present invention provides a method of producing a polar ester compound represented by the following Reaction Scheme 1.

[Reaction Scheme 1]

-continued

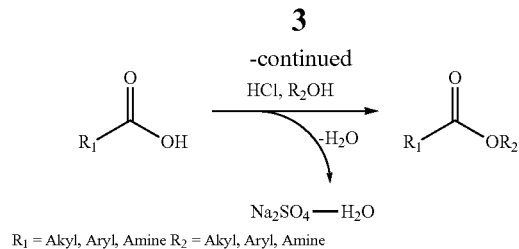

$R_1$ = Akyl, Aryl, Amine $R_2$ = Akyl, Aryl, Amine

In Reaction Scheme 1, magnesium chloride ($MgCl_2$) may be any one selected from among a hydrate and an anhydride, $R_1$ may be selected from among organic acids having a C1-C20 alkyl group, an aromatic functional group, or an amine functional group, and $R_2$ may be selected from among primary, secondary, and tertiary alcohols.

In addition, in the method of producing a polar ester compound, an ethyl acetate solvent is additionally used in the esterification reaction.

More preferably, in the method of producing a polar ester compound, the carboxylic acid and the alcohol are lauric acid and ethanol, respectively.

In addition, in the method of producing a polar ester compound, the carboxylic acid and the alcohol may be acetic acid and menthol, respectively.

In addition, in the method of producing a polar ester compound, the carboxylic acid and the alcohol may be gallic acid and ethanol, respectively.

In addition, in the method of producing a polar ester compound, the carboxylic acid and the alcohol may be arginine and ethanol, respectively.

Meanwhile, another aspect of the present invention provides ethyl lauroyl arginate produced through an acylation reaction by treating arginine ethyl ester, which is a polar ester compound produced using the arginine and the ethanol, with lauroyl chloride.

However, the objectives of the present invention are not limited to those described above, and any means for achieving the above-described objectives within the range that can be understood by a person skilled in the art according to the description of the present invention will be included in the scope of the present invention.

Advantageous Effects

According to the present invention, it is possible to reduce the risk of hazardous material generation and explosion compared to the conventional esterification reaction, and since the difficulty of removing a catalyst during purification and the problem of hydrolysis caused by water generated during the reaction can be improved, a conversion rate to esters can be increased, and thus an ester compound can be produced in high yields.

Moreover, since an alkali metal salt or an alkaline earth metal salt which is obtainable from seawater and can be easily purchased on the market at an affordable price is used, the process cost can be lowered, and since hazardous waste is not generated, environmental problems can be improved.

In addition, compared to the conventional esterification reaction, the ester compound is produced in high yields and a purification method is simple, so the unit cost of a product can be lowered when the method of the present invention is commercially used.

MODES OF THE INVENTION

Figure 1:
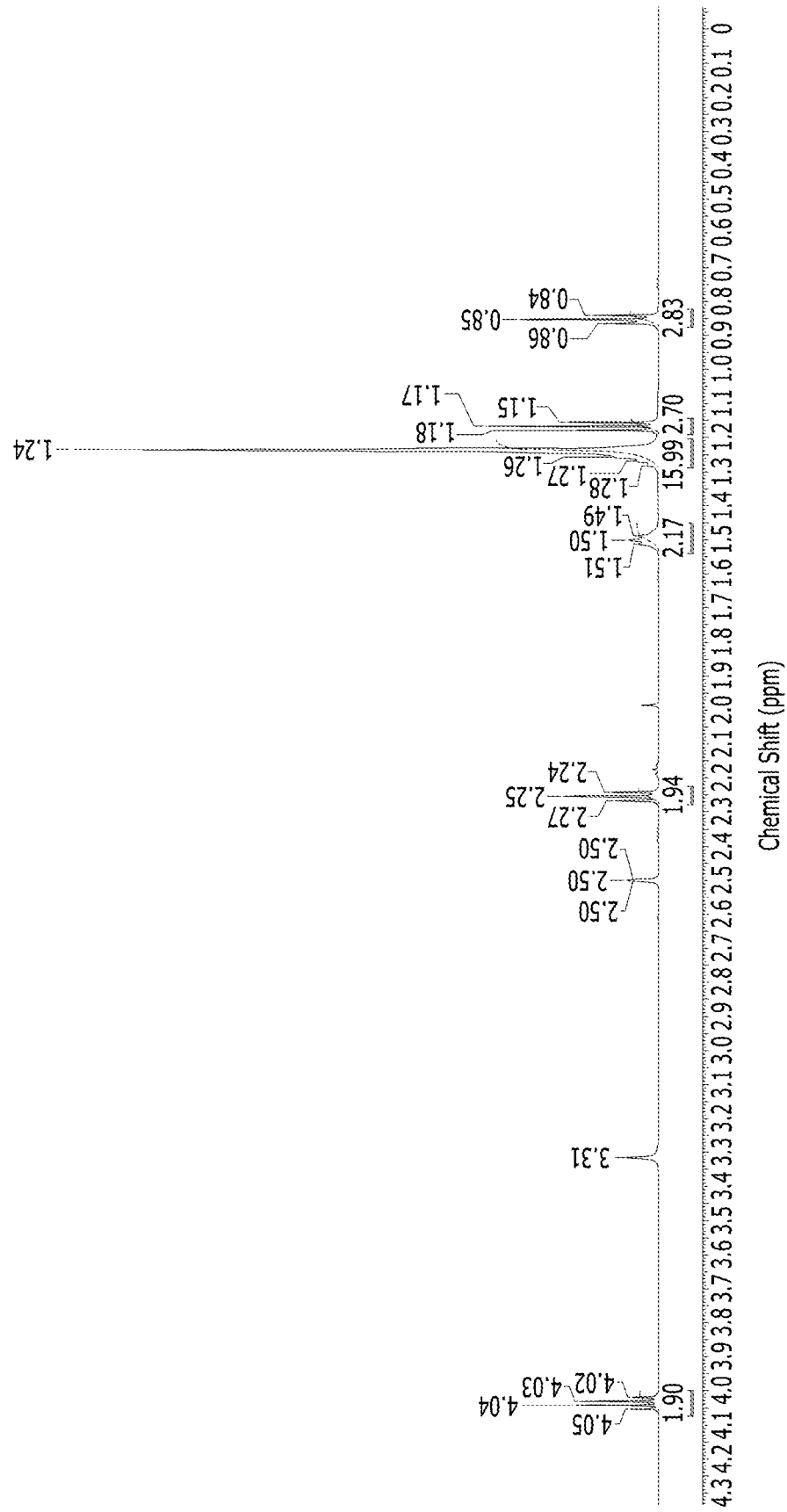
FIG. 1 is an $^1H$ NMR spectrum of a reaction product produced according to a method of producing ethyl laurate (Example 1).

Hereinafter, a more detailed technical background will be first described before describing specific details for carrying out the present invention.

The present invention has a technical background in which hydrochloric acid is produced by the ion exchange between sulfuric acid and magnesium chloride, which is a constituent of seawater, and water is removed using sodium sulfate, and this technical background is illustrated in Reaction Schemes 1 and 2.

[Reaction Scheme 1]

$MgCl_2 + H_2SO_4 \longrightarrow MgSO_4 + 2\ HCl$

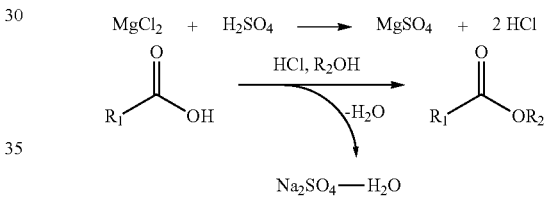

In Reaction Scheme 1, magnesium chloride ($MgCl_2$) may be any one selected from among a hydrate and an anhydride, $R_1$ may be selected from among organic acids having a C1-C20 alkyl group, an aromatic functional group, or an amine functional group, and $R_2$ may be selected from among primary, secondary, and tertiary alcohols.

In general, since sulfuric acid has low reactivity with a solid metal salt, it is important that the metal salt is ionized. However, since typical metal chlorides have low solubility in alcohols and thus cannot be completely dissociated, it is preferable that the metal chlorides are provided in the form of hydrates. However, in this case, since a hydrolysis reaction, which is the reverse reaction of the esterification reaction, is induced, it is required that a dehydrating agent for removing water is added.

In Reaction Scheme 1, the magnesium sulfate produced by the reaction of magnesium chloride and sulfuric acid acts as a dehydrating agent for removing water and thus satisfies the above-described condition, but in this case, since the reaction time may be increased or hydrolysis may occur due to a solvent and water in a reaction tank, it is preferable to separately add anhydrous sodium sulfate as a dehydrating agent. However, whether anhydrous sodium sulfate should be added depends on the characteristics of the product. Specifically, when the product is susceptible to a hydrolysis reaction, anhydrous sodium sulfate should be added to better secure water molecules, but when the product is not susceptible to a hydrolysis reaction, it is not necessary to add anhydrous sodium sulfate.

For the esterification reaction, it is ideal to use hydrochloric acid, but since hydrochloric acid is in a gaseous state, there is the inconvenience of having to inject hydrochloric acid gas at regular intervals during the reaction. In addition, since hydrochloric acid gas is relatively expensive and difficult to handle, it is not efficient in terms of economic efficiency and process convenience.

Therefore, in the reaction represented by Reaction Scheme 1, hydrochloric acid gas is generated due to the chloride ions derived from magnesium chloride and the hydrogen ions derived from sulfuric acid, and since an esterification reaction proceeds using the hydrochloric acid as an acid catalyst, the above-described problems can be easily solved.

In addition, when an amino acid is used as a reactant, an amino acid ester, which is a product, becomes a basic compound due to an amine because zwitterion equilibrium is not established, and in this case, the basic compound forms an ammonium salt with an acid catalyst, causing the catalyst to be used up. As a result, the pH of the reaction system may be increased, and since the amount of catalyst has decreased, a forward reaction is not induced, and thus a yield is reduced. Therefore, since it is required to use more acid catalyst, it is very difficult to remove the residual catalyst during purification. In addition, there are disadvantages that, since the salt form of this amino acid ester has a high degree of polarity, it is very difficult to extract and purify the same, and since an acid catalyst also has a high degree of polarity, it is very difficult to purify the acid catalyst with high purity and high efficiency.

The present invention has advantages in that since hydrochloric acid gas is generated due to the ion exchange between a chloride and a sulfur oxide and water molecules are removed by a dehydrating agent, a conversion rate to esters is high, and since hydrochloric acid gas, which can be easily removed, is used as an acid catalyst, purification can be easy with only a single filter.

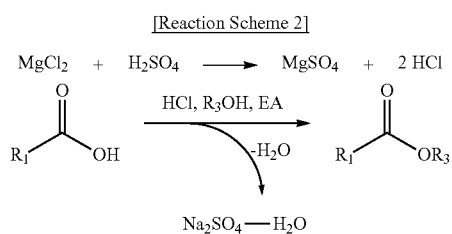

[Reaction Scheme 2]

In Reaction Scheme 2, $R_1$ may be selected from among organic acids having a C1-C20 alkyl group, an aromatic functional group, or an amine functional group, and $R_3$ may be selected from among primary, secondary, and tertiary alcohols.

The esterification reaction is a condensation reaction between a branched alcohol (e.g., a secondary alcohol or a tertiary alcohol) or a primary alcohol and an organic acid. Such a reaction is typically used when producing a fragrance, and ester compounds into which various branched alcohols are introduced are relatively highly priced. This is not only due to the relatively high price of the branched alcohols, but also because the branched alcohols have a lower conversion rate to esters than primary alcohols. Another reason is that since the branched alcohols are hydrolyzed relatively quickly under acidic conditions and thus cannot be easily produced through a general esterification reaction, an expensive reagent is required for the production thereof. In addition, since high temperature is typically required, a solvent having a high boiling point, such as toluene, is used. However, solvents having a high boiling point, including toluene, have high toxicity, cannot be easily purified, and have residual solvent problems.

In order to solve these problems, in the present invention, an esterification reaction between a branched alcohol and an organic acid is induced, using ethyl acetate (EA) as a solvent, based on a reaction in which the hydrochloric acid gas catalyst generated by salt ion-exchange and water are removed. The EA used herein is a safe solvent produced by a condensation/esterification reaction of ethanol and acetic acid, and does not cause environmental pollution and is capable of inducing a safe reaction. Moreover, EA is capable of stably producing an ester compound based on a branched alcohol despite having a low boiling point of 77.1° C. and is economical because the used EA can be reused.

Ester compounds suitable for commercialization have been manufactured by the method of the present invention, and representative compounds are shown in Reaction Schemes 3 to 7.

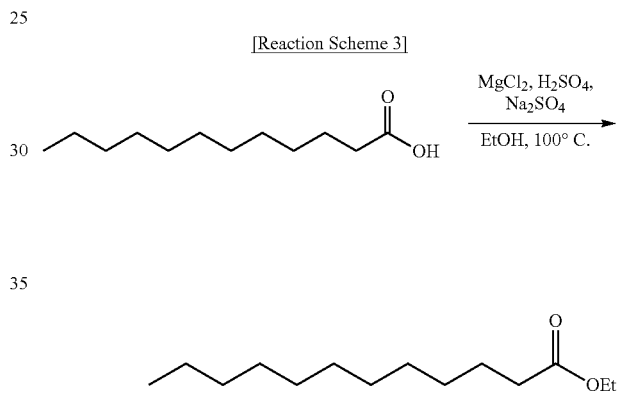

Ethyl laurate, which is produced by a condensation reaction of lauric acid and ethanol, is an oily ester compound having a characteristic odor. This material is a fatty acid ester compound and also one of the main components of biodiesel, and is used as a fragrance. This reaction is carried out using lauric acid, sulfuric acid, and magnesium chloride hydrate in a molar ratio of 1:2.5:2.75. When sulfuric acid and magnesium chloride are reacted in a ratio of 1:1, two hydrochloric acid molecules are produced. Since two hydrochloric acid molecules are not sufficient for lowering a pKa value that affects a conversion rate to esters, at least twice the equivalent is required. In addition, when sulfuric acid and magnesium chloride are reacted, the sulfuric acid should be the limiting reactant, and this is because as all of the sulfuric acid is consumed to form magnesium sulfate and magnesium hydrogen sulfate, residual sulfuric acid can be easily removed. In addition, in order to remove the water contained in magnesium chloride, the amount of sodium sulfate should be adjusted to be the same amount as the water so that the water can be quickly removed.

As shown in Reaction Scheme 3, the ethyl laurate produced by the method of the present invention can be purified by a simple method and has a high conversion rate to esters, and has no hazardous waste, so the ethyl laurate can be applied to an environmentally-friendly biodiesel manufacturing method.

[Reaction Scheme 4]

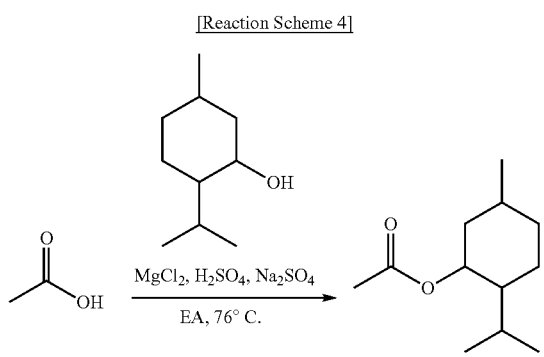

Menthol used in Reaction Scheme 4 is used as a fragrance, and there are several types of fragrances produced based on menthol. Among them, a menthol derivative produced by applying the present invention is menthyl acetate.

Menthyl acetate can be obtained by a condensation reaction of menthol and acetic acid, but in the conventional technique, menthyl acetate is produced using menthyl chloride or acetyl chloride. However, since an excessive amount of acetyl chloride or acetic acid is required, or thionyl chloride should be used when preparing an alkyl chloride or an acyl chloride, the generation of hazardous materials throughout the process is inevitable. In particular, since the type of solvent used for the reaction is limited, and in all cases, the reaction proceeds under harmful solvent conditions such as toluene and benzene, the method is environmentally inappropriate.

In the present invention, EA, which is a solvent that does not cause environmental pollution, is used as a solvent, and the menthol used herein is unrefined menthol obtained from nature and is used to prepare menthyl acetate. In addition, the menthyl acetate is produced using 1.6 moles of acetic acid per mole of the menthol used herein, that is, without using an excessive amount of acetic acid, and this is because a menthol-based compound is highly soluble in an organic solvent but is not easily dissolved in water during purification and thus is not easily separated during purification. On the other hand, acetic acid is easily dissolved in a basic aqueous solution and thus is easily separated, so even when menthol acetate is produced using an increased number of moles of acetic acid, the unreacted acetic acid can be easily removed. In addition, since menthol, which is a secondary alcohol, is not only highly hydrolyzable and the menthol used herein is in the form of an unrefined mixture in which there may be other low-molecular-weight alcohols present, at least 3.5 equivalents of each of sulfuric acid, magnesium chloride hydrate, and magnesium sulfate are used to carry out the reaction.

The reason for using unrefined menthol extracted from nature in the present invention is to solve the problem encountered by cosmetic manufacturers. Fragrances are added in most cosmetics, but may include allergenic components such as linalool and geranial. While using raw materials listed in the green grade of the Environmental Working Group (EWG), which is the consumer's purchasing standard, is a recent trend and a marketing factor in the cosmetic industry, these allergenic components of fragrances do not meet the green grade, so solving the problem of the fragrances remains an important task. In order to solve this problem, essential oils extracted from natural sources have been used as substitutes, but the compounds responsible for the fragrance of essential oils have the same structures as the allergens in artificial fragrances and thus should be labeled as allergens under current law. Since compounds such as linalool and geranial are alcohol-based compounds having a R—OH functional group, problems thereof can be solved through esterification, and since ester-based compounds are the main components responsible for the fragrance of most fruits and flowers, the ester-based compounds are suitable for use in the cosmetic industry. In particular, essential oils containing large amounts of linalool and geranial are widely used in the cosmetics industry, and when the essential oils, which are mixtures, are esterified with fatty acids, the essential oils are converted into ester-based compounds and thereby can easily meet the detection criteria for allergens. For this reason, in the present invention, an ester compound is produced using unrefined menthol extracted from nature.

[Reaction Scheme 5]

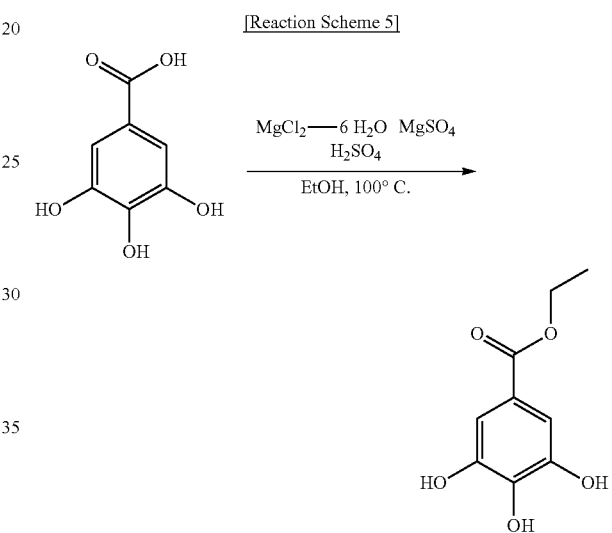

Gallic acid used in Reaction Scheme 5 is known to have a very strong antioxidant effect. In particular, due to having the strong antioxidant ability, gallic acid is used for enhancing nutrition and as a preservative for preventing oxidation of food. However, since gallic acid may readily undergo browning due to having the strong antioxidant ability, in order to provide the protective effect while securing an ester structure, gallic acid that has a safe and stable ethyl ester structure has been used. Since, in pure gallic acid, electrons freely move between a hydroxyl group and a carboxylic acid group which are in a para (p-) relationship with each other in the aromatic ring and cause rapid browning, various alkyl esters are introduced, of which ethyl groups are suitable as protecting groups because they are not hazardous when broken down in vivo. In the reaction represented by Reaction Scheme 5, gallic acid monohydrate, sulfuric acid, and magnesium chloride hydrate are used in a molar ratio of 1:2:2.2, and since gallic acid has a structure having a high conversion rate to esters, it is possible to use smaller amounts of sulfuric acid and magnesium chloride hydrate.

When ethyl gallate is produced by applying the esterification reaction of the present invention, hazardous and toxic materials commonly used in the conventional technique are not used, and hazardous waste is not generated, so it has an advantage in commercial production.

[Reaction Scheme 6]

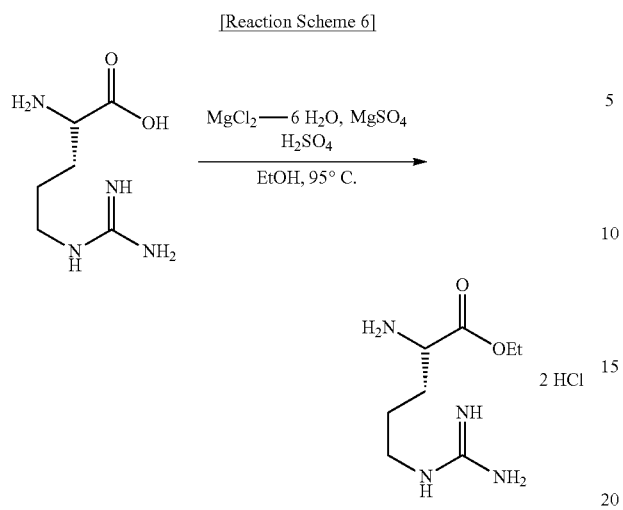

[Reaction Scheme 7]

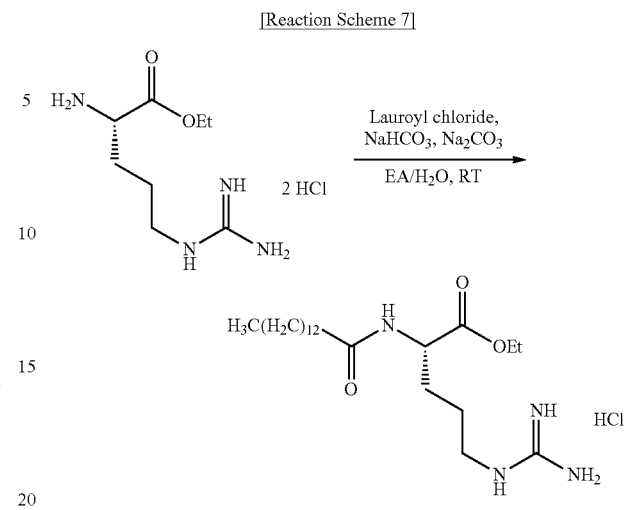

Arginine used in Reaction Scheme 6 is classified as a basic amino acid among the 20 amino acids and is one of the building blocks of a protein. Arginine has various functions such as preventing vascular disease, healing wounds, and preventing kidney disease and thus is widely used as a nutrient fortifying agent.

However, since the absorption rate of arginine is low, arginine is administered in the form of an ethyl ester, and this is because the absorption rate of the ethyl ester form is higher. In addition, since arginine ethyl ester is a synthetic intermediate of ethyl lauroyl alginate (ELA) which is a sterilizing preservative for foods, cosmetics, and pharmaceuticals and a multifunctional bioactive material, a high value-added material can be manufactured. However, when basic amino acids are subjected to an esterification reaction, an acid catalyst is used up, resulting in a low conversion rate to esters, which leads to excessive use of the catalyst, and the use of an excessive amount of toxic materials poses an unavoidable risk of environmental pollution and human toxicity. In addition, it is difficult to purify by separating basic amino acids from residual acid catalysts, so there is a disadvantage of low economic efficiency. Moreover, arginine ethyl ester has very low solubility in a non-aqueous organic solvent used for purification, and thus there is a disadvantage that it is very difficult to purify arginine ethyl ester by removal of residual catalysts and impurities. In the reaction represented by Reaction Scheme 6, arginine, sulfuric acid, and magnesium sulfate are used in a molar ratio of 1:3:3.3. Since arginine is strongly basic and thus consumes one hydrochloric acid molecule, and the product, arginine ethyl ester, consumes one additional hydrochloric acid molecule, at least six hydrochloric acid molecules are required. Therefore, at least three equivalents of sulfuric acid are required to satisfy the low pKa condition for increasing a conversion rate.

According to the present invention, hazardous materials are not generated even when an excessive amount of catalyst is used, and since a conversion rate to esters is high, arginine ester can be easily produced without the difficulty of purification and the difficulty caused by a low yield. Moreover, since environmental waste and toxic waste are not generated, there is also the advantage of low waste treatment costs, and the method can be widely used commercially.

Reaction Scheme 7 shows a method of producing ethyl lauroyl arginate hydrochloride (ELA) using the arginine ethyl ester produced by the above-described esterification reaction of the present invention. ELA can be produced by an acylation reaction with lauroyl chloride using arginine ethyl ester as a starting material.

ELA is a sterilizing preservative for foods, cosmetics, and pharmaceuticals and has a broad spectrum of potent antibacterial and antiviral functions. In addition, ELA has various functions, including breaking down toxic materials secreted by bacteria, softening skin and hair, and adsorbing onto the surface of the human body to prevent the adhesion of bacteria.

However, in the conventional process, due to the problem of an esterification reaction which is a first step and the low yield and purity resulting from the hydrolysis occurring in an acylation reaction, ELA is highly priced and thus has not been easily popularized.

The esterification reaction of the present invention reduces the process cost of the first step through high efficiency and environmental friendliness, and at the same time, reduces the probability of hydrolysis by using a carbonate buffer solution in the acylation reaction, thereby solving all the problems of the conventional ELA manufacturing process.

The reactions represented by Reaction Schemes 1 and 2, which are the technical core of the present invention, have been described above, and hereinafter, the present invention will be described by way of specific examples. The five Examples described below illustrate processes of producing compounds suitable for various purposes using various organic acids and two types of alcohols as starting materials and a method of producing another high value-added ester compound using the produced materials.

[Example 1] Production of Ethyl Laurate

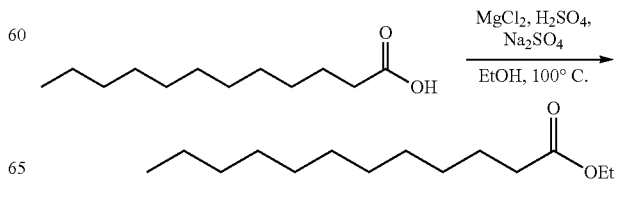

1. To a 1,000 mL round-bottom flask, 600 mL of EtOH and 140 g of $MgCl_2 \cdot 6H_2O$ were added and dissolved, and then 50 g of lauric acid was added.
2. After stirring the resultant of step 1 for 20 minutes, 97 g of $Na_2SO_4$ was added, and then 33 mL of $H_2SO_4$ was slowly added.
3. The resultant of step 2 was stirred for six hours while maintaining a temperature of 100° C.
4. The reaction mixture was cooled to room temperature, filtered, and then concentrated.
5. After dissolving the resultant of step 4 by adding 100 mL of EA, an organic layer was washed once with a saturated aqueous $NaHCO_3$ solution.
6. The resultant of step 5 was dehydrated with $Na_2SO_4$, filtered, and then concentrated, and thereby ethyl laurate (54 g, 95%) in the form of a pale yellow oil was obtained.

The following is the results of analyzing the obtained ethyl laurate compound by $^1$H NMR after step 6, and the spectrum is shown in FIG. 1.

$^1$H NMR (600 MHz, DMSO-d6) δ4.05-4.02 (q, 2H), 2.27-2.24 (t, 2H), 1.51-1.49 (t, 2H), 1.24 (s, 16H), 1.18-1.15 (t, 3H), 0.86-0.84 (t, 3H)

[Example 2] Production of Menthyl Acetate

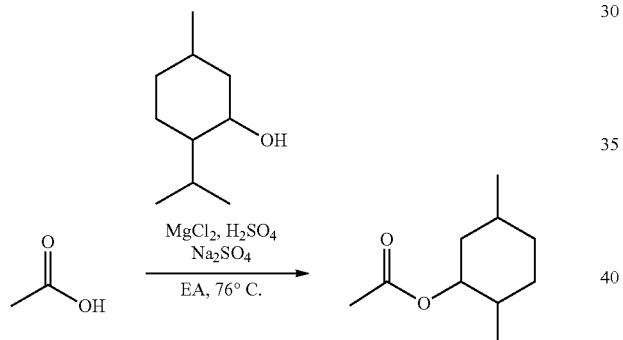

1. To a 1,000 mL round-bottom flask, 300 mL of EA and 8 mL of AcOH were added and dissolved, and then 72 g of $MgCl_2 \cdot 6H_2O$ was added.
2. After stirring the resultant of step 1 for 20 minutes, 20 g of menthol (unrefined raw material extracted from a natural source) and 97 g of $Na_2SO_4$ were added, and then 33 mL of $H_2SO_4$ was slowly added.
3. The resultant of step 2 was stirred for 18 hours while maintaining a temperature of 76° C.
4. The reaction mixture was cooled to room temperature, filtered, and then concentrated.
5. After dissolving the resultant of step 4 by adding 100 mL of EA, an organic layer was washed once with a saturated aqueous $NaHCO_3$ solution.
6. The resultant of step 5 was dehydrated with $Na_2SO_4$, filtered, and then concentrated, and thereby menthyl acetate (17 g, 96%) in the form of a yellow oil was obtained.

Figure 2:
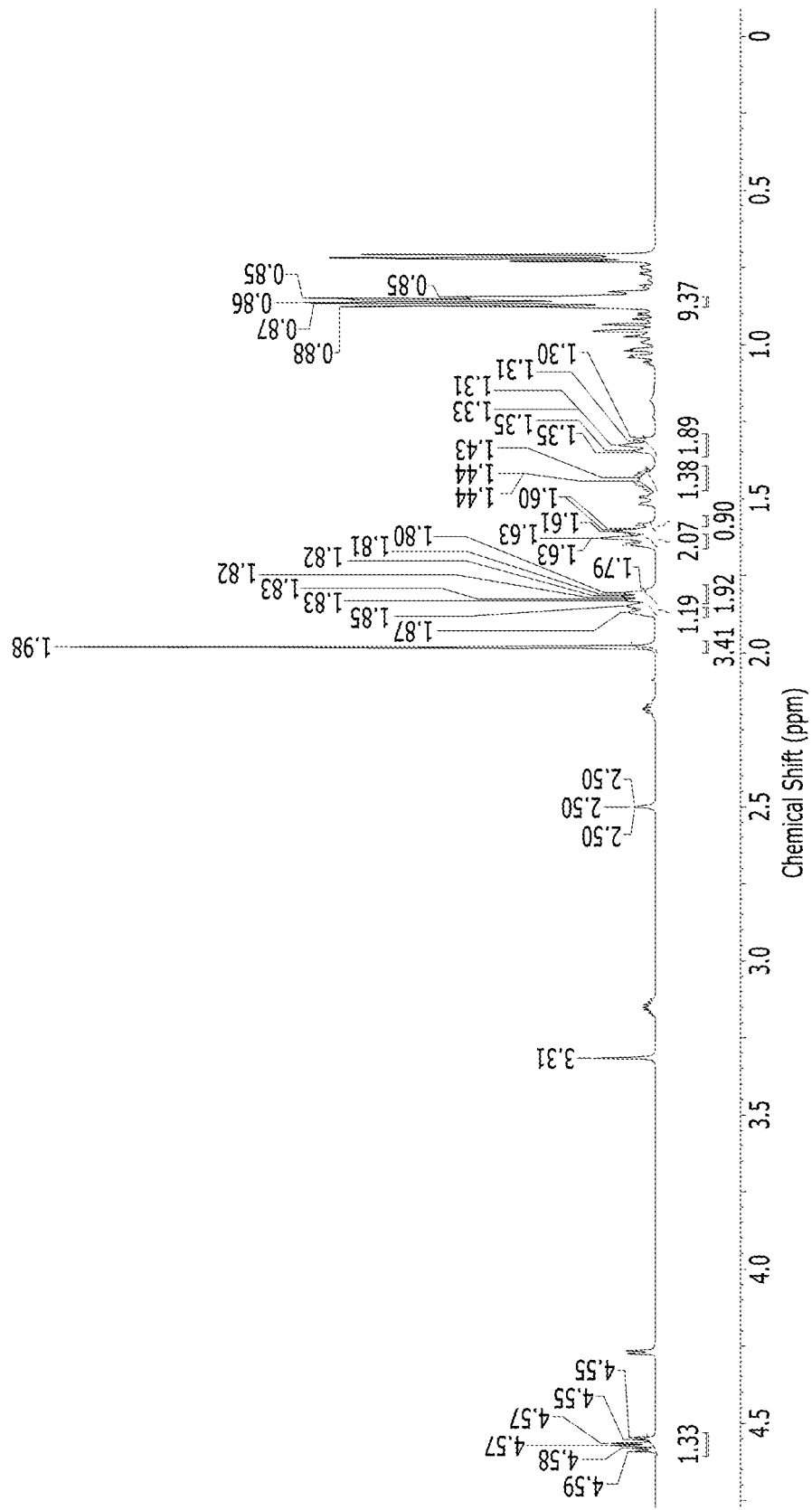
FIG. 2 is an $^1H$ NMR spectrum of a reaction product produced according to a method of producing menthyl acetate (Example 2).

The following is the results of analyzing the obtained menthyl acetate compound by $^1$H NMR after step 6, and the spectrum is shown in FIG. 2.

$^1$H NMR (600 MHz, DMSO-d6) δ4.59-4.55 (m, 1H), 1.98 (s, 3H), 1.87-1.83 (m, 11H), 1.82-1.79 (m, 2H), 1.65-1.61 (m, 2H), 1.60-1.58 (m, 1H), 1.48-1.40 (m, 1H), 1.37-1.30 (m, 2H), 0.88-0.85 (m, 9H)

[Example 3] Production of Ethyl Gallate Using Desalting and Salt Substitution Method

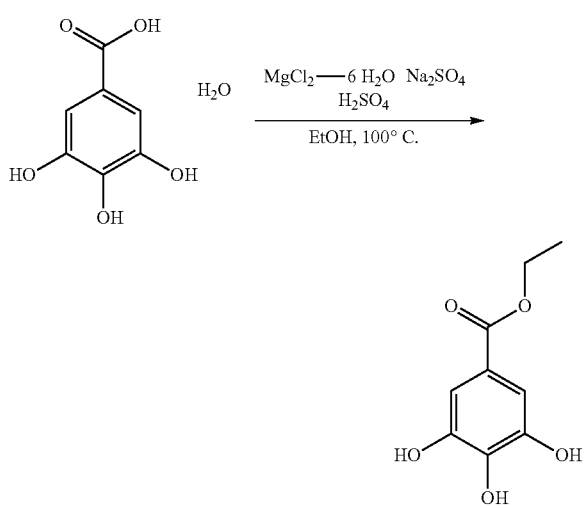

1. To a 1,000 mL round-bottom flask, 500 mL of EtOH and 119 g of $MgCl_2 \cdot 6H_2O$ were added and dissolved, and then 50 g of gallic acid·$H_2O$ was added.
2. After stirring the resultant of step 1 for 20 minutes, 83 g of $Na_2SO_4$ was added, and then 28 mL of $H_2SO_4$ was slowly added.
3. The resultant of step 2 was stirred for 12 hours while maintaining a temperature of 100° C.
4. The reaction mixture was cooled to room temperature and then filtered, and the filtrate was concentrated, and thereby ethyl gallate (52 g, 98%) in the form of a white solid was obtained.

Figure 3:
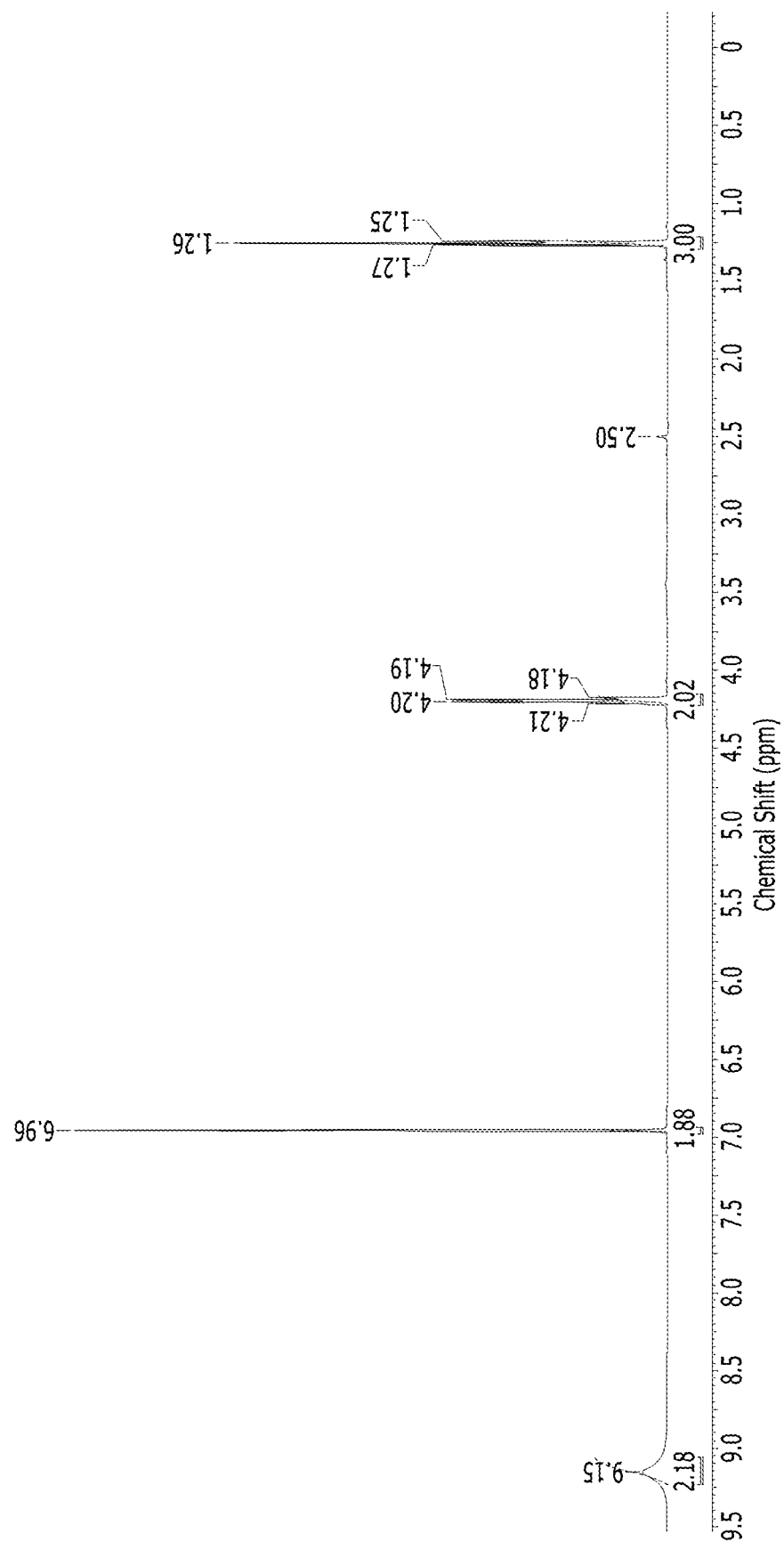
FIG. 3 is an $^1H$ NMR spectrum of a reaction product produced according to a method of producing ethyl gallate (Example 3).

The following is the results of analyzing the obtained ethyl gallate compound by $^1$H NMR after step 4, and the spectrum is shown in FIG. 3.

$^1$H NMR (600 MHz, DMSO-d6) δ9.15 (brs, 2H), 9.96 (s, 2H), 4.21-4.18 (q, 2H), 1.27-1.25 (t, 3H)

[Example 4] Production of Arginine Ethyl Ester Dihydrochloride

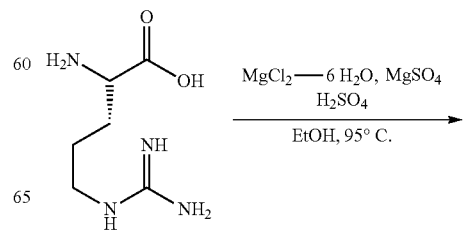

-continued

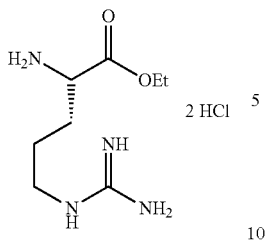

1. To a 1,000 mL round-bottom flask, 600 mL of EtOH and 193 g of MgCl$_2$·6H$_2$O were added and dissolved, and then 50 g of arginine was added.
2. After stirring the resultant of step 1 for 20 minutes, 135 g of Na$_2$SO$_4$ was added, and then 46 mL of H$_2$SO$_4$ was slowly added.
3. The resultant of step 2 was stirred for 18 hours while maintaining a temperature of 95° C.
4. The reaction mixture was cooled to room temperature and then filtered, and the filtrate was concentrated, and thereby arginine ethyl ester dihydrochloride (77 g, 97.5%) in the form of a white solid was obtained.

Figure 4:
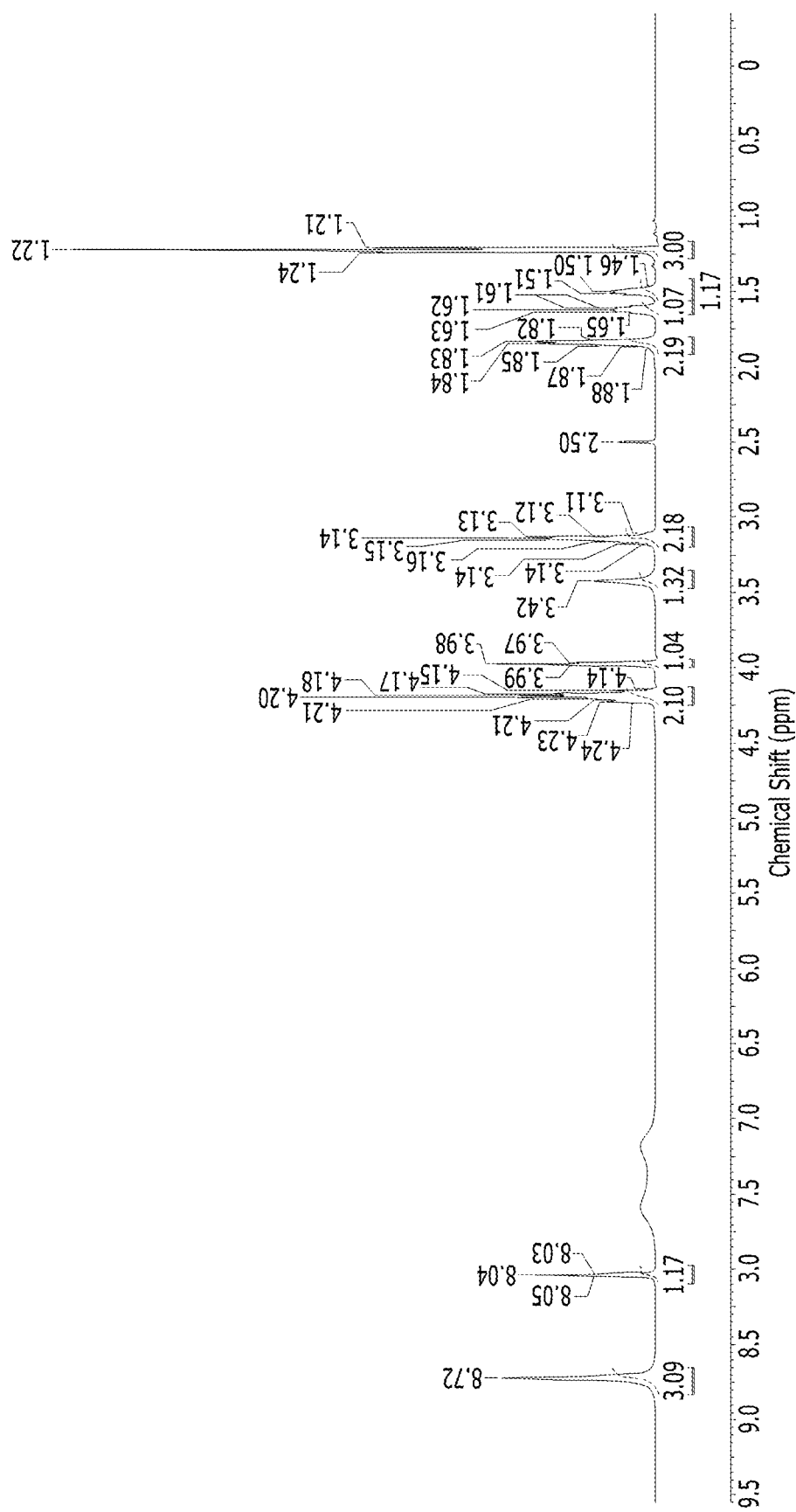
FIG. 4 is an $^1H$ NMR spectrum of a reaction product produced according to a method of producing arginine ethyl ester dihydrochloride (Example 4).

The following is the results of analyzing the obtained arginine ethyl ester dihydrochloride compound by $^1$H NMR after step 4, and the spectrum is shown in FIG. 4.

$^1$H NMR (600 MHz, DMSO-d6) δ8.72 (s, 3H), 8.05-8.03 (t, 1H), 4.24-4.14 (m, 2H), 3.99-3.97 (t, 1H), 3.42 (brs, 1H), 3.19-3.11 (m, 2H), 1.88-1.80 (m, 2H), 1.66-1.59 (m, 1H), 1.53-1.46 (m, 1H), 1.24-1.21 (t, 3H)

[Example 5] Production of Ethyl Lauroyl Arginate Hydrochloride

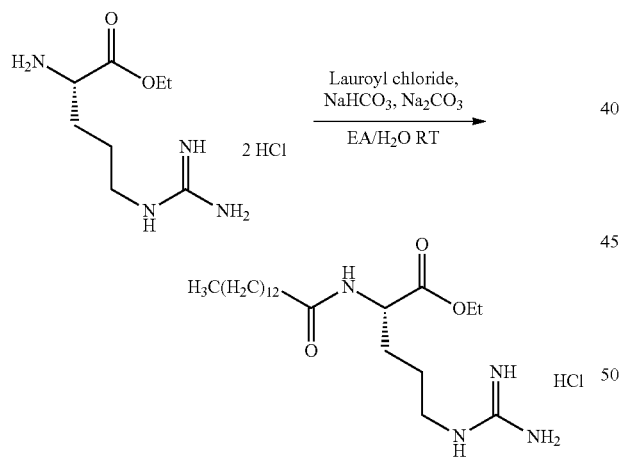

1. To a 1,000 mL round-bottom flask, 150 mL of distilled water and 60 g of arginine ethyl ester dihydrochloride were added and dissolved, and the resultant was stirred at room temperature.
2. To the resultant of step 1, an aqueous solution prepared by dissolving 23.1 g of Na$_2$CO$_3$ and 1.8 g of NaHCO$_3$ in 200 mL of distilled water was added, and then 350 mL of EA was added.
3. To the resultant of step 2, 51 mL of lauroyl chloride was slowly added, and the mixture was stirred for three hours at room temperature.
4. After removing an aqueous layer, 200 mL of brine and then 10 mL of hydrochloric acid (>35%) were added to an organic layer and then stirred for five minutes.
5. After removing an aqueous layer, an organic layer was cooled to a temperature of 4° C. or less and then filtered, and thereby ethyl lauroyl arginate hydrochloride (88 g, 96%) in the form of white needle-shaped crystals was obtained.

Figure 5:
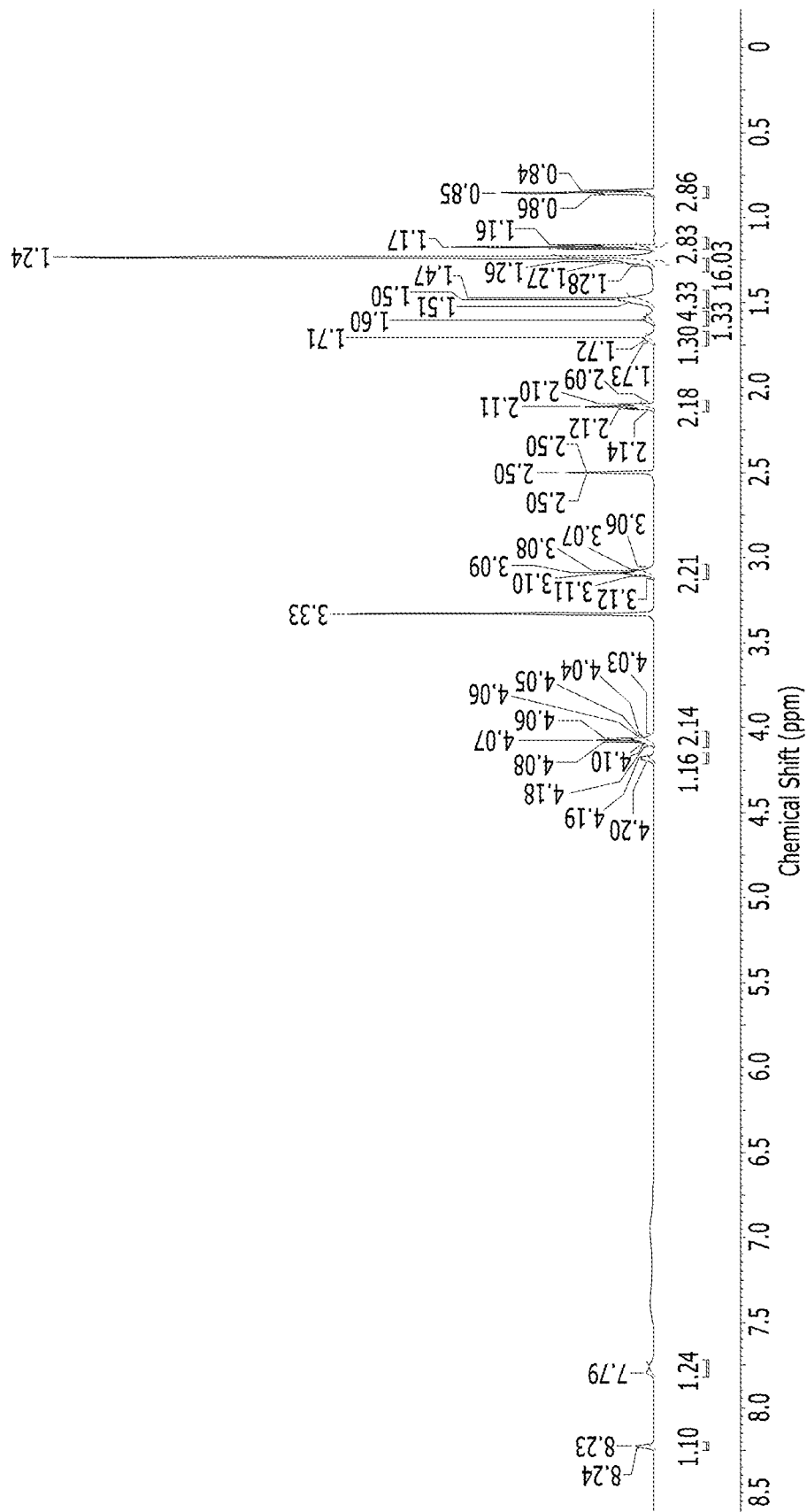
FIG. 5 is an $^1H$ NMR spectrum of a reaction product produced according to a method of producing ethyl lauroyl arginate hydrochloride (Example 5).
Figure 6:
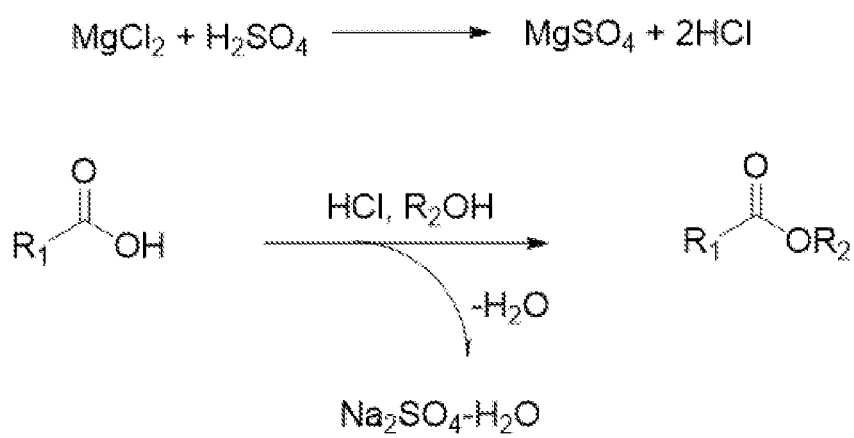
FIG. 6 shows Reaction Scheme 1 of the present invention.

The following is the results of analyzing the obtained ethyl lauroyl arginate hydrochloride compound by $^1$H NMR after step 5, and the spectrum is shown in FIG. 5.

$^1$H NMR (600 MHz, DMSO-d6) δ8.24-8.23 (brd, 1H), 7.79 (brs, 1H), 4.20-4.16 (m, 1H), 4.11-4.03 (m, 2H), 3.12-3.06 (brs, 2H), 2.14-2.09 (m, 2H), 1.74-1.68 (m, 1H), 1.63-1.56 (m, 1H), 1.63-1.46 (m, 4H), 1.28-1.24 (m, 16H), 1.19-1.16 (t, 3H), 0.86-0.84 (t, 3H)

The present invention has the advantage of solving the problems of the conventional esterification reaction, such as the use of hazardous materials, the difficulty of removing residual catalysts, the generation of hazardous gas, the generation of toxic waste, and a low conversion rate to esters due to the difficulty of removing water during a dehydration process. In addition, since both polar products and non-polar products can be produced, and purification is relatively easy, and a material in an inexpensive salt form is used, an ester compound can be manufactured in an economical way.

The invention claimed is:

1. A method of manufacturing an ester compound based on an esterification reaction using a salt ion-exchange method represented by the following Reaction Scheme 1:

[Reaction Scheme 1]

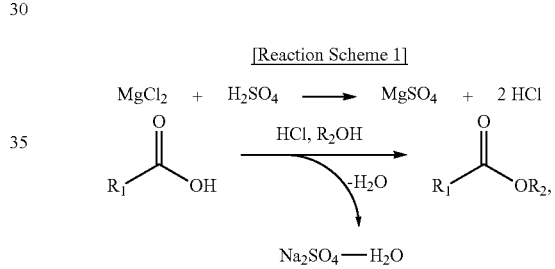

wherein the reaction is carried out in a single reaction tank, and
wherein, in the Reaction Scheme 1:
the magnesium chloride (MgCl$_2$) is a hydrate;
the hydrochloric acid (HCl) is used as a catalyst in esterification reaction;
the R$_1$(C=O)OH is selected from among organic acids having a C1-C20 alkyl group, an aromatic functional group, or an amine functional group;
the R$_2$OH is selected from among primary, secondary, and tertiary alcohols; and
the magnesium sulfate (MgSO$_4$) acts as a dehydrating agent for removing water.

2. The method of claim 1, wherein an ethyl acetate (EA) solvent is additionally used in the esterification reaction.

3. The method of claim 1, wherein the R$_1$(C=O)OH and the R$_2$OH are lauric acid and ethanol, respectively.

4. The method of claim 2, wherein the R$_1$(C=O)OH and the R$_2$OH are acetic acid and menthol, respectively.

5. The method of claim 1, wherein the R$_1$(C=O)OH and the R$_2$OH are gallic acid and ethanol, respectively.

6. The method of claim 1, wherein the R$_1$(C=O)OH and the R$_2$OH are arginine and ethanol, respectively.

* * * * *